United States Patent [19]

Bonham et al.

[11] Patent Number: 5,187,045
[45] Date of Patent: Feb. 16, 1993

[54] HALOMETHYL-1,3,5-TRIAZINES CONTAINING A SENSITIZER MOIETY

[75] Inventors: James A. Bonham; Mitchell A. Rossman, both of St. Paul, Minn.

[73] Assignee: Minnesota Mining and Manufacturing Company, St. Paul, Minn.

[21] Appl. No.: 710,103

[22] Filed: Jun. 4, 1991

Related U.S. Application Data

[60] Division of Ser. No. 508,370, Apr. 11, 1990, Pat. No. 5,034,526, which is a continuation-in-part of Ser. No. 241,319, Sep. 7, 1988, abandoned.

[51] Int. Cl.$^5$ .......................... G03F 7/031; G03F 7/09
[52] U.S. Cl. .................................. 430/275; 430/271; 430/281; 430/283; 430/284; 430/916; 430/920; 522/63; 522/34; 522/50; 522/913
[58] Field of Search ............... 430/281, 916, 920, 284, 430/283, 275, 271; 522/63, 34, 50, 913

[56] References Cited

U.S. PATENT DOCUMENTS

| | | | |
|---|---|---|---|
| 3,495,987 | 2/1970 | Moore | 96/115 |
| 3,617,288 | 11/1971 | Hartman et al. | 96/90 |
| 3,640,718 | 2/1972 | Smith | 96/89 |
| 3,729,313 | 4/1973 | Smith | 96/27 R |
| 3,779,778 | 12/1973 | Smith et al. | 96/115 R |
| 3,905,815 | 9/1975 | Bonham | 96/68 |
| 3,954,475 | 5/1976 | Bonham | 96/67 |
| 3,987,037 | 10/1976 | Bonham | 260/240 D |
| 4,181,752 | 1/1980 | Martens et al. | 427/54.1 |
| 4,189,323 | 2/1980 | Buhr | 430/281 |
| 4,228,232 | 10/1980 | Rousseau | 430/271 |
| 4,239,850 | 12/1980 | Kita et al. | 430/281 |
| 4,259,432 | 3/1981 | Kondoh et al. | 430/281 |
| 4,391,687 | 7/1983 | Vesley | 204/159.16 |
| 4,476,215 | 10/1984 | Kausch | 430/281 |
| 4,505,793 | 3/1985 | Tamoto et al. | 204/159.16 |
| 4,758,497 | 7/1988 | Shah et al. | 430/191 X |
| 4,933,452 | 6/1990 | White et al. | 544/204 |

FOREIGN PATENT DOCUMENTS

| | | |
|---|---|---|
| 0109291 | 6/1984 | European Pat. Off. |
| 0341720 | 11/1989 | European Pat. Off. |
| 2851641 | 5/1979 | Fed. Rep. of Germany |
| 3517440 | 11/1986 | Fed. Rep. of Germany |
| 60-60104 | 4/1985 | Japan |

OTHER PUBLICATIONS

Ko Wakabayashi et al., "Studies on s-Triazines. I. Co-trimerization of Trichloroacetonitrie with Other Nitriles", *Bulletin of The Chemical Society of Japan*, vol. 42, 1969, pp. 2924–2930.

Ulrich von Gizyeki, "Isocyanato-s-Triazines", *Angewante Chemie*, Int'l Edn Eng. 1971, p. 403.

Jaromir Kosar, *Light–Sensitive Systems: Chemistry and Application of Nonsilver Halide Photographic Process* (John Wiley & Sons, Inc., N.Y., 1965) pp. 361–370.

*Primary Examiner*—Cynthia Hamilton
*Attorney, Agent, or Firm*—Gary L. Griswold; Walter N. Kirn; David L. Weinstein

[57] ABSTRACT

Radiation-sensitive organo-halogen compounds having a photo-labile halomethyl-1,3,5-triazine moiety and at least one sensitizer moiety within one molecule. The compounds of this invention are good photoinitiators, and compositions containing them can be used in printing, duplicating, copying, and other imaging systems.

20 Claims, No Drawings

HALOMETHYL-1,3,5-TRIAZINES CONTAINING A SENSITIZER MOIETY

This is a division of 508,370, filed Apr. 11, 1990, now U.S. Pat. No. 5,034,526 which is a continuation-in-part of U.S. Ser. No. 07/241,319, filed Sep. 7, 1988, now abandoned.

BACKGROUND OF THE INVENTION

1. Field of Invention

The present invention relates to photosensitive compounds that generate free radicals upon exposure to light. More particularly, it relates to derivatives of halomethyl-1,3,5-triazines.

2. Discussion of the Prior Art

Compounds that decompose to generate free radicals (free radical generating agents) upon exposure to light are well known in the graphic arts. Organic halogen compounds, which are capable of generating free radicals such as a chlorine free radical or a bromine free radical upon exposure to light, have been widely used as photoinitiators in photopolymerizable compositions, as photoactivators in free radical photographic compositions, and as photoinitiators for reactions catalyzed by acids formed by light. The spectral sensitivity of these compositions may be broadened by the addition of sensitizers which, in essence, transfer their absorbed energy to the organic halogen compound. The use of such halogen compounds in photopolymerization processes and free radical photographic processes have been described in Kosar, *Light-Sensitive Systems*, J. Wiley & Sons (New York, 1965) pp. 180-181, 361-370.

Halomethyl-1,3,5-triazines are known to be initiators for a number of photochemical reactions. They are employed to produce free radicals for initiating polymerization or color changes and for initiating secondary reactions upon liberation of acid by the interaction of the free-radicals when hydrogen donors are present.

Examples of the use of halomethyl-1,3,5-triazines in the free radical polymerization of acrylate monomers are described in U S. Pat. No. 3,905,815; U.S. Pat. No. 3,617,288; U.S. Pat. No. 4,181,752; U.S. Pat. No. 4,391,687; U.S. Pat. No. 4,476,215; and DE 3,517,440. U.S. Pat. No. 3,779,778 discloses the photoinitiated acid catalyzed decomposition of pyranyl ether derivatives to produce photosolubilizable compositions useful as positive printing plates. Chromophore substituted styryl-1,3,5-triazines and their uses are disclosed in U.S. Pat. No. 3,987,037 and U.S. Pat. No. 3,954,475. Radiation sensitive compositions containing bi- and polyaromatic substituted triazines are disclosed in U.S. Pat. No. 4,189,323.

In compositions, the sensitivity of halomethyl-1,3,5-triazines to actinic radiation of a particular range of wavelengths can be increased by the incorporation of known ultraviolet and visible light sensitizers including cyanine, carbocyanine, merocyanine, styryl, acridine, polycyclic aromatic hydrocarbons, polyarylamines and amino-substituted chalcones. Cyanine dyes are described in U.S. Pat. No. 3,495,987. Styryl dyes and polyarylamines are described in Kosar, *Light Sensitive Systems*, J. Wiley and Sons (New York, 1965), pages 361-369. Polycyclic aromatic hydrocarbons useful as sensitizers, an example of which is 2-ethyl-9,10-dimethoxyanthracene, are described in U.S. Pat. No. 3,640,718. Amino substituted chalcones useful as sensitizers are described in U.S. Pat. No. 3,617,288. Halomethyl-1,3,5-triazines are used in conjunction with dialkylamino aromatic carbonyl compounds disclosed in U.S. Pat. No. 4,259,432; 2-(benzoylmethylene)-5-benzothiazolidene thiazole -4-1 compounds disclosed in E application 0109291, May 23, 1984; 3-keto-substituted coumarin compounds disclosed in U.S. Pat. No. 4,505,793; U.S. Pat. No. 4,239,850; Jpn. Kokai Tokkyo Koho JP 60 60,104 (85 60104); an Ger/ Offen 2,851,641.

SUMMARY OF THE INVENTION

This invention provides radiation-sensitive organohalogen compounds that have good sensitivity in the ultraviolet and visible range of the spectrum, and are thus suitable for use in radiation-sensitive compositions. These compounds have a photo-labile halomethyl-1,3,5-triazine moiety and a sensitizer moiety within one molecule, thereby eliminating the need for a combination of compounds. In this fashion, the efficiency of transfer of energy between the sensitizer moiety and the triazine moiety is increased on account of the decreased physical distance between the two moieties. The compounds of this invention are good photoinitiators. Photopolymerizable and photocrosslinkable compositions containing them can be used in printing, duplicating, copying, and other imaging systems.

This invention provides compounds having a 1,3,5-triazine moiety having at least one halomethyl substituent on one carbon atom of the triazine nucleus, preferably a trihalomethyl group, and at least one sensitizer moiety on another carbon atom of the triazine nucleus, said sensitizer moiety not being part of the triazine chromophore, said sensitizer moiety being capable of absorbing actinic radiation, said sensitizer moiety having a λmax (i.e., absorption maximum) of at least 330 nm, preferably 350 nm up to 900 nm. The presence of the sensitizer moiety gives the compounds of this invention greater spectral sensitivity than halomethyl-1,3,5-triazine compounds not having such a sensitizer moiety. Representative examples of sensitizer groups include cyanine group, carbocyanine group, merocyanine group, aromatic carbonyl group, styryl group, acridine group, polycyclic aromatic hydrocarbyl group, polyarylamine group, amino-substituted chalcone group, etc.

The compound is capable of stimulation by actinic radiation at a wavelength of about 250 to 900 nanometers to generate free radicals or acids or both. These compounds are useful as photoreaction initiators for photosensitive compositions. They can be incorporated in photopolymerizable compositions and printing compositions useful for producing printing plates, such as lithographic plates, relief plates, or gravure plates, photoresists and photographic elements, and photosensitive resist forming compositions with which visible images are obtained upon exposure to light.

DETAILED DESCRIPTION OF THE INVENTION

As used herein, the term "sensitizer moiety" means a moiety containing at least one group that is not a part of the triazine chromophore and is capable of absorbing actinic radiation and enhancing spectral sensitivity.

Halomethyl substituted, 1,3,5-triazine compounds of this invention can be represented by the general formula I:

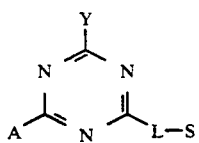

wherein

A represent a member selected from the group consisting of mono-, di- and trihalo methyl groups, Y represent a member selected from the group consisting of A, L-S, $NH_2$, NHR, $NR_2$, OR, and R', where R independently represents a substituted or unsubstituted alkyl group, preferably having 1 to 6 carbon atoms, or a substituted or unsubstituted aryl group, and R' represents a substituted or unsubstituted alkyl group, preferably having 1 to 6 carbon atoms, a substituted or unsubstituted aryl group, a substituted or unsubstituted alkenyl group, preferably having 2 to 6 carbon atoms, or a substituted or unsubstituted heterocyclic aromatic group, S represents a sensitizer moiety that is not part of the triazine chromophore and is capable of absorbing actinic radiation, S having a λmax of at least 330 nm, and L represents a group linking the sensitizer moiety to the triazine nucleus.

Halomethyl groups that are suitable for the present invention include chloro-, bromo-, and iodomethyl groups, with chloro- and bromomethyl groups being preferred. Trihalomethyl groups are preferred; most preferred are trichloromethyl and tribromomethyl groups.

Y represents any of a variety of substituents that are useful in modifying the physical, e.g., solubility, or chemical properties of the molecule, and preferably represents A, L-S, or R'. When Y represents A, the maximum number of halomethyl groups per triazine nucleus can be made available for radical generation. When Y represents L-S, the chemical composition for both L-S groups can be the same, or it can be different, depending on the composition of linking group L, sensitizer group S, or both. When Y represents R', and in particular when R' represents an aryl, aralkenyl, or heteroaromatic group, the spectral sensitivity of the triazine chromophore portion of the molecule can be varied, based on the photochemical response of R, to actinic radiation.

When R or R' represents an aryl group it is preferred that the group have a maximum of five rings, more preferably three rings, and most preferably one ring.

When R or R' represents a substituted group, the particular identity of the substituent is not critical. However, the substituents should not adversely affect the photoinitiation characteristics of the compounds of this invention.

S represents a sensitizer-containing group which, by itself, would not initiate photopolymerization upon exposure to actinic energy, but is nevertheless capable of absorbing actinic radiation, and transferring energy to the halomethyl-1,3,5-triazine moiety, thereby effectively increasing the spectral sensitivity of the halomethyl-1,3,5-triazine moiety. The sensitizer moiety has a λmax (i.e., absorption maximum) of at least 330 nm, preferably 350 nm up to 900 nm. S preferably comprises at least one member selected from the group consisting of cyanine group, carbocyanine group, merocyanine group, aromatic hydrocarbon group, polyarylamine group, and amino-substituted chalcone group. There is no upper limit on the number of sensitizer moieties per triazine nucleus; there is no upper limit on the number of triazine nuclei per sensitizer moiety; however, there must be at least one sensitizer moiety and at least one triazine nucleus. Preferably, the number of sensitizer moieties per triazine nucleus ranges from one to two or two to one; more preferably, there is one sensitizer moiety per triazine nucleus. If more than one sensitizer moiety is present per triazine nucleus, they can be from different generic classes or can be different species from the same generic class. If there is more than one triazine nucleus per sensitizer moiety, they can be of the same or of different species.

L represents a group that links the sensitizer moiety or moieties to the triazine nucleus. The precise identity of L is not critical, but it should be selected so that it does not interfere with or adversely affect the light sensitivity of the compound. Furthermore, L should be chosen so that it does not connect the chromophore of the halomethyl-1,3,5-triazine nucleus and the chromophore of the sensitizer moiety either directly by a covalent bond or by a conjugated linkage. However, any through space intramolecular complexation between the chromophores is not precluded. L can be a single group or can be formed from a combination of groups. Groups that are suitable for linking groups include carbamator ($-NHCO_2-$), urea ($-NHCONH-$), amino ($-NH-$), amido ($-CONH_2-$), aliphatic e.g., having up to 10 carbon atoms, alkyl, e.g., having up to 10 carbon atoms, alkenyl, e.g., having up to 10 carbon atoms, aryl, e.g., having one ring, styryl, ester ($-CO_2-$), ether ($-O-$), and combinations thereof. Based on ease of synthesis, the most preferred groups for attachment directly to the triazine nucleus are carbamato, urea, amino, alkenyl, aryl, and ether. Whenever the group directly attached to the triazine nucleus is either alkenyl group or aryl group, another group must be interposed between the alkenyl group or aryl group and the sensitizer moiety to prevent the sensitizer moiety from forming a conjugate bond with the triazine nucleus.

The following structures exemplify typical —L—S combinations:

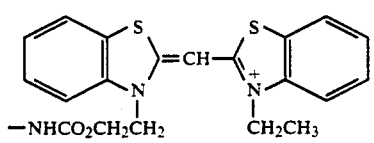

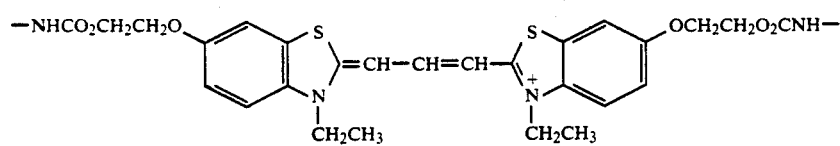
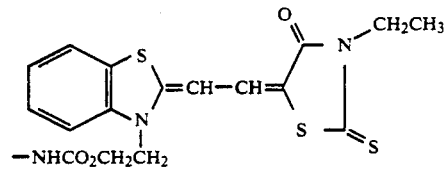
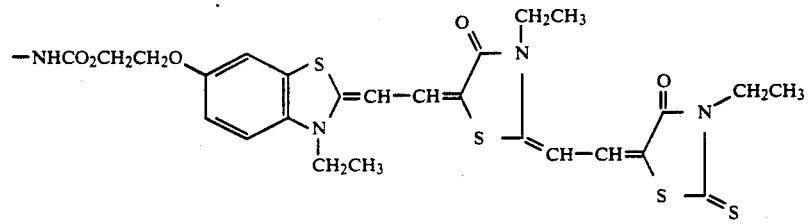
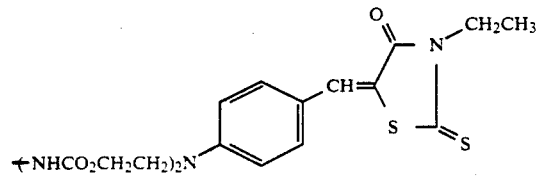
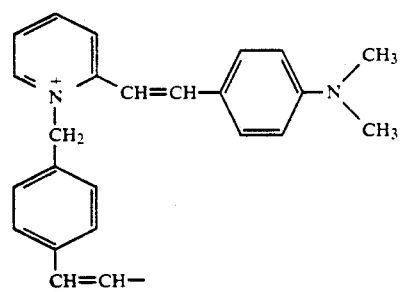
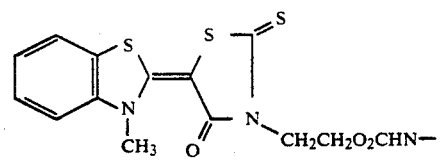
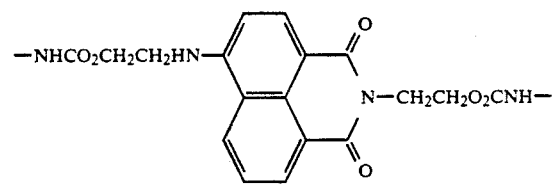
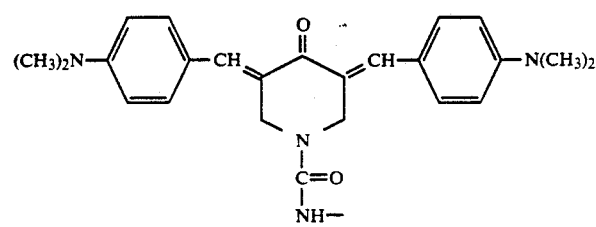

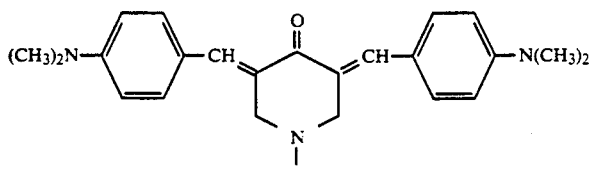

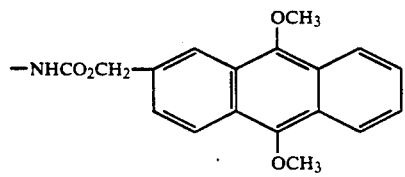

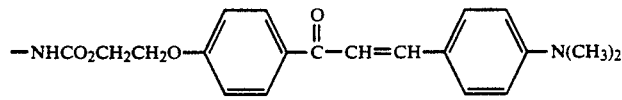

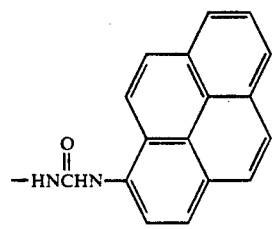

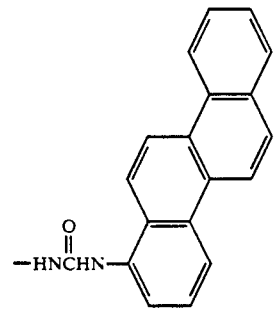

One method of preparing the compounds of this invention is by the addition reaction of isocyanato-substituted halomethyl-1,3,5-triazines with sensitizers having groups reactive with the isocyanate group. The isocyanato substituted triazines may be prepared from the corresponding amino derivative according to the procedure of U. Von Gizycki, Angew, Chem. Int. Ed. Eng., 1971, 10, 403. Isocyanato-1,3,5-triazines suitable for this reaction include:

2,4-bis(trichloromethyl)-6-isocyanato-1,3,5-triazine 2-isocyanato-4-methyl-6-trichloromethyl-1,3,5-triazine 2-isocyanato-4-phenyl-6-trichloromethyl-1-3,5-triazine 2-isocyanato-4-methoxy-6-trichloromethyl-1,3,5-triazine 2-isocyanato-4-(p-methoxyphenyl)-6-trichloromethyl-1,3,5-triazine 2-isocyanato-4-(p-methoxystyryl)-6-trichloromethyl-1,3,5-triazine 2-isocyanato-4-(m,p,-dimethoxyphenyl)-6-trichloromethyl-1,3,5-triazine 2,4,6-tris(isocyanato)-1-3,5-triazine Examples of sensitizers that will combine with the isocyanto group include 4-(2'-hydroxyethyl)amino-N-2''-hydroxyethyl)-1,8-naphthalimide, 3,5-bis(dimethylaminobenzal)-4-piperidone, hydroxyethylrhodanine-N'''-methylbenzothiazole, 1-aminopyrene, and 6-aminochrysene.

The isocyanate addition reaction can be carried out in the presence of solvents, such as, for example, toluene, pyridine, benzene, xylene, dioxane, tetrahydrofuran, etc., and mixtures of solvents. The duration and temperature of the reaction is dependent on the particular compounds and the catalyst employed. Generally, temperatures of about 25° to 150° for from one to seventy-two hours are sufficient to provide for the reaction. Preferably, the reaction is carried out at room temperature from three to seventy-two hours. The preferred catalyst is di-n-butyltin dilaurate.

Another method of preparing the compounds of this invention is the cotrimerization of organic nitriles having a sensitizer substituent with haloacetonitriles in accordance with the teachings of Wakabayashi et al, Bulletin of the Chemical Society of Japan, 1969, 42, 2924-30; still another method of preparing the compounds of this invention is the condensation reaction of an aldehyde compound having a photoinitiator functionality in accordance with the teachings of U.S Pat. No. 3,987,037; still another method of preparing the compound of this invention is the nucleophilic displacement reactions on halomethyl-1,3,5-triazines using sensitizers having free hydroxy or amino groups.

The natural sensitivity of halomethyl-1,3,5-triazines to actinic radiation is well known. Simple derivatives, such as 2-methyl-4,6-bistrichloromethyl-1,3,5-triazine, absorb actinic radiation in the lower ultraviolet region, e.g. below 300 nm.

Photosensitizers have been added to compositions containing halomethyl-1,3,5-triazines as separate materials to, in effect, broaden their natural range of sensitivity. This phenomenon is complex, and is believed to involve various types of energy transfer mechanisms from the excited states of the sensitizer. Moreover, the efficiency of physical combinations of sensitizing dye and photoinitiator is limited due to concentration, solubility, and light filtration factors. The compounds of this invention in which the sensitizer moiety and the halomethyl-1,3,5-triazine moiety are in the same molecule are more efficient for several reasons. They eliminate the need to add each material separately. They assure that the sensitizer moiety is very close to the triazine nucleus, thereby allowing lower concentrations and increased energy transfer efficiency.

A halomethyl-1,3,5-triazine compound having a chromophore substituted directly to the triazine nucleus has a broader sensitivity range than the unsubstituted halomethyl-1,3,5-triazine compound. See, for example, U.S. Pat. No. 3,954,475, U.S. Pat. No. 4,189,323, U.S. Pat. No. 4,391,687, and DE 3517440. However, the nature of the compounds in these patents is limited in that preparation thereof requires formation of a covalent bond or a conjugated linkage between the triazine nucleus and the chromophore substituent, typically by either an aryl group or a vinyl group. Because the triazine nucleus is not insulated from the chromophore substituent, it is difficult to predict, a priori, the absorption characteristics, i.e., absorption maxima, of the resulting chromophore-triazine combination because they will differ from those of both the chromophore and the triazine.

The compounds of this invention provide a wide variety of structures in that dye and triazine precursors can be prepared independently and then synthetically combined by simple reactions and without having to form a conjugated linkage. Also, the spectral sensitivity can be predicted, a priori, to correspond to the spectral sensitivity of the sensitizer moiety. By utilizing a sensitizer moiety having a λmax (i.e., absorption maximum) of at least 330 nm, the range of sensitivity of a halomethyl-1,3,5-triazine compound can be broadened.

Photopolymerizable compositions wherein the compounds of this invention can be used typically comprise (1) an unsaturated, free radical initiated, chain propagating addition polymerizable compound, (2) a compound of this invention, and (3) optionally, one or more fillers, binders, dyes, polymerization inhibitors, color precursors, oxygen scavengers, etc. The compounds of this invention should be present in an amount sufficient to initiate polymerization of said polymerizable compound. Suitable ratios of ingredients are as follows: for every 100 parts of polymerizable compound there can be from 0.005 to 10 parts of photoinitiator, from 0 to 200 parts of filler, from 0 to 200 parts of binder, and from 0 to 10 or more parts of dyes, polymerization inhibitors, color precursors, oxygen scavengers, etc, as may be needed for a particular use of the photopolymerizable compositions. Preferably, from 1 to 7.5 parts of the compound of this invention and from 25 to 150 parts of binder are used per 100 parts of polymerizable compound.

Unsaturated, free-radical initiated, chain-propagating addition polymerizable compounds suitable for the compositions of this invention include alkylene or polyalkylene glycol diacrylates, e.g., ethylene glycol diacrylate, diethylene glycol diacrylate, glycerol diacrylate, glycerol triacrylate, ethylene glycol dimethacrylate, 1,3-propanediol dimethacrylate, 1,2,4-butanetriol trimethacrylate, 1,4-cyclohexanediol diacrylate, pentaerythritol tetramethacrylate, pentaerythritol triacrylate, sorbitol hexacrylate; bis[1-(3-acryloxy-2-hydroxy)]-p-propoxyphenyl dimethylmethane, bis[1-(2-acryloxy)]-p-ethoxyphenyldimethylmethane, tris hydroxyethylisocyanurate trimethacrylate, the bis-acrylate and the bis-methacrylates of polyethylene glycols of molecular weight 200–500 and the like; unsaturated amides, e.g., methylene bis-acrylamide, methylene bis-methacrylamide, 1,6-hexamethylene bis-acrylamide, diethylene triamine trisacrylamide, beta-metha-crylaminoethyl methacrylate; vinyl esters such as divinyl succinate, divinyl adipate, divinyl phthalate, the preferred unsaturated compounds being pentaerythritol tetracrylate, bis[p-(3-acryloxy-2-hydroxypropoxy)phenyl]dimethylmethane, and bis[p-(2-acryloxyethoxy)phenyl]-dimethylmethane. Mixtures of these esters can also be used as can mixtures of these esters with alkyl esters of acrylic acid and methacrylic acid, including such esters as methyl acrylate, methyl methacrylate, ethyl acrylate, isopropyl methacrylate, n-hexyl acrylate, stearyl acrylate, allyl acrylate, diallyl phthalate, and the like.

To prepare the photosensitive compositions of this invention, the components can be admixed in any order and stirred or milled to form a solution or uniform dispersion. Photosensitive elements can be made by coating a photosensitive composition on a suitable base or support and drying the coating. The dry thickness typically ranges from about 0.00005 to about 0.075 inch.

Suitable bases or supports for the photosensitive compositions include metals, e.g., steel and aluminum plates, sheets and foils, and films or plates composed of various film-forming synthetic or high polymers including addition polymers, e.g. vinylidene chloride, vinyl chloride, vinyl acetate, styrene, isobutylene polymers and copolymers and linear condensation polymers e.g., polyethylene terephthalate, polyhexamethylene adipate, polyhexamethylene adipamide/adipate.

The invention will be more specifically illustrated by the following examples. The value of λmax was measured in methanol, unless otherwise indicated.

EXAMPLE 1

This example illustrates preparation of 4-amino-[2'-ethyl-N'-(4,6-bistrichloromethyl)-1,3,5-triazin-2-yl)-carbamate]-N-[2'-ethyl-N"-(4,6-bis(trichloromethyl)-1,3,5-triazin-2-yl)-carbamate]-1,8-naphthalimide. To a solution containing 345 mg (1.1 mmol)-4-(2'-hydroxyethyl-)amino-N-(2"-hydroxyethyl)-1,8-napthalimide in 50 ml dry toluene was added a solution of 1.17 g (3.4 mmol) 2,4-bis(trichloromethyl)-6-isocyanato1,3,5-triazine in 8 ml dry toluene. The reaction mixture was stirred under N$_2$ at 25° C. for six days. The solvent was removed by means of a rotary evaporator under reduced pressure and the residue was loaded upon a silica gel column (100 g packed in dichloromethane) and eluted with dichloromethane. The fractions containing the bright yellow compound were collected and the solvent was removed to yield 320 mg product (29% yield). The product had a melting point in excess of 260° C. and a λmax of 433 nm. The structure of this product is shown below.

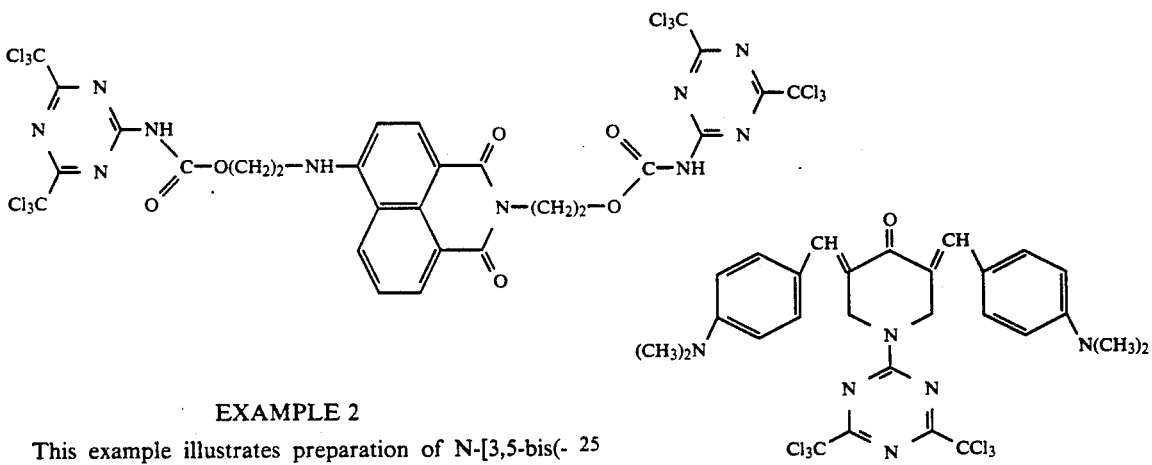

EXAMPLE 2

This example illustrates preparation of N-[3,5-bis(-dimethylaminobenzal)-4-piperidone]-[4,6-bis)trichloromethyl)-1,3,5-triazin-2-yl]carbamate. To a solution containing 2.20 g (5.6 mmol) 3,5-bis(dimethylaminobenzal)-4-piperidone and 20 drops di-n-butyltin dilaurate in 200 ml dry dichloromethane was added 2.0 g (5.6 mmol) 2,4-bis(trichloromethyl)-6-isocyanato-1,3,5-triazine. The reaction mixture was stirred at room temperature under a nitrogen atmosphere for 24 hours. The solvent was removed by means of a rotary evaporator under reduced pressure at room temperature. The residue was treated with 20 ml dichloromethane and the precipitate was filtered and dried to yield a 3.38 g product (84% yield). The product had a melting point in excess of 260° C. and a λmax of 460 nm. The structure of this product is shown below.

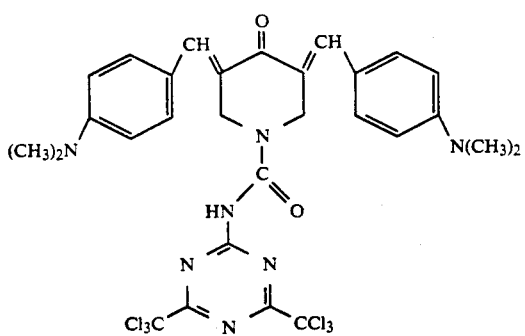

EXAMPLE 3

This example illustrates preparation of 2-[3',5'-bis(-dimethylaminobenzal)-4'-piperidone]-4,6-bis(trichloromethyl)-1,3,5-triazine. A solution containing 414 mg (1.2 mmol) 3,5-bis(dimethylaminobenzal)-4-piperidone and 500 mg (1.2 mmol) 2,4,5-tris(trichloromethyl)-1,3,5-triazine in 150 ml methanol was heated to reflux for 62 hours. The reaction mixture was cooled to room temperature, and the precipitate was filtered and dried to yield 385.4 mg product (53% yield). The product had a melting point in excess of 260° C. and λmax of 455 nm. The structure of this product is shown below.

EXAMPLE 4

This example illustrates preparation of 2-(hydroxyethylrodanine-N''-methylbenzothiazole)-N'[4,6-bis(trichloromethyl)-1,3,5-triazin-2-yl]-carbamate. To a solution containing 90.8 mg (2.8 mmol) hydroxyethylrodanine-N''-methylbenzothiazole in 50 ml dry toluene was added 158.3 mg (5.0 mmol) 2,4-bis(trichloromethyl)-6-isocyanato-1,3,5-triazine. The reaction mixture was stirred at room temperature under a nitrogen atmosphere for 45 hours. The solvent was removed by means of a rotary evaporator under reduced pressure at room temperature. The residue was treated with a small amount of dichloromethane and the resulting precipitate was filtered to yield 118.8 mg product (62% yield). The product had a melting point of 185°-189° C. and a λmax of 428 nm. The structure of this product is shown below.

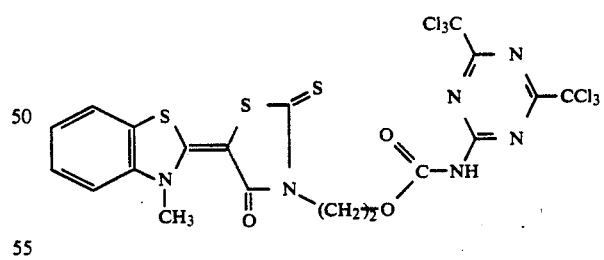

EXAMPLE 5

This example illustrates preparation of N-[1'-pyrene]-N'-[4,6-bis(trichloromethyl)-1,3,5-triazin-2-yl]-urea. To a solution containing 500 mg (2.3 mmol) 1-aminopyrene and 20 drops di-n-butyltin dilaurate in 50 ml dry toluene was added 815 mg (2.3 mmol) 2,4-bis(trichloromethyl)-6-isocyanato-1,3,5-triazine. The reaction mixture was stirred at room temperature under a nitrogen atmosphere for 17.5 hours. The precipitate was filtered and dried to yield 1.11 gm product (84% yield). The product had a melting point of 244°-246° C. and a λmax of 340 nm. The structure of this product is shown below.

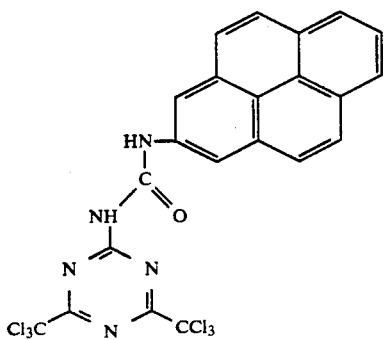

EXAMPLE 6

This example illustrates preparation of N-[6'-chrysene]-N'-[4,6-bis(trichloromethyl)-1,3,5-triazin-2-yl]-urea. To a solution containing 250 mg (1.0 mmol) 6-aminochrysene and 20 drops of di n-butyltin dilaurate in 50 ml dry toluene was added 365 mg (1.0 mmol) 2,4-bis(trichloromethyl)-6-isocyanto-1,3,5-triazine. The reaction mixture was stirred at room temperature under a nitrogen atmosphere for 17.5 hours. The precipitate was filtered and dried to yield 354 mg product (60% yield). The product had a melting point of 238°–241° C. and a λmax of 330 nm. The structure of this product is shown below.

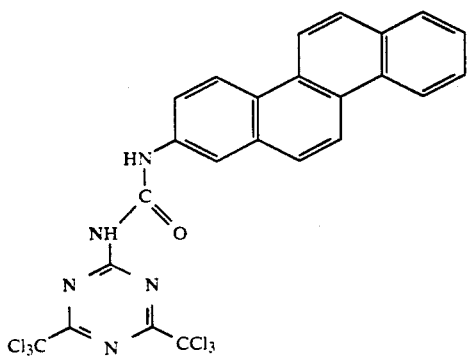

EXAMPLE 7

This example illustrates the preparation of photosensitive elements using the halomethyl-1,3,5-triazines of this invention and the spectral response of the compounds in such elements.

A solution was prepared from 74.24 g azeotrope of 1-propanol and water (71.8% 1-propanol/28.2% water), 4.32 g pentaerythritol tetraacrylate ("SARTOMER" monomer SR-295, Arco Chemical Company), 5.64 g oligomer (prepared according to U.S. Pat. No. 4,228,232 and 60.9% in methyl ethyl ketone), 0.30 g triethylamine, and 14.88 g a 1:1 mixture of polyvinyl acetate-methylal resin ("FORMVAR" 12/85T, Union Carbide Corp.) and red pigment (Pigment Red 48, C.I. 15865) (9.4% by weight solution of the azeotrope). To 2.5 g of this solution was added 10–15 mg initiator, and the resulting solution shaken in the dark for 15 minutes. The solution was filtered through glass wool and coated onto a grained, anodized aluminum plate with a #12 Mayer bar. The plate was dried at 66° C. for 2 min and cooled to room temperature. To this coating was applied a topcoat formulation (prepared from 5.00 g carboxymethyl cellulose ether (CMC-7L), 0.26 g surfactant ("TRITON" X-100 (10% in water)), and 95.00 g water) with a #14 Mayer bar, and the topcoat carefully dried with a heat gun. The plates were exposed for 5 sec in air on top of a draw-down glass in a 3M Seventy unit equipped with a 2 kw photopolymer bulb through a √2, 21 step Stouffer step tablet. The plates were soaked in a developer solution prepared from 784.4 g deionized water, 16.7 g sodium metasilicate pentahydrate, 33.4 g 1-propanol, and 0.5 surfactant ("DOWFAX-2A1", Dow Chemical Company (45% solution in water)) for 15 sec and rubbed 10 times with a 4 in.×4 in. cotton pad. The relative sensitivities for triazines are shown in Table 2.

TABLE 2

| Initiator | Solid Step |
|---|---|
| Example 1 | 5 |
| Example 2 | 9 |
| Example 3 | 5 |
| Example 4 | 3 |
| Example 5 | 3 |
| Example 6 | 3 |

Various modifications and alterations of this invention will become apparent to those skilled in the art without departing from the scope and spirit of this invention, and it should be understood that this invention is not to be unduly limited to the illustrated embodiments set forth herein.

What is claimed is:

1. A radiation-sensitive composition comprising: (1) an ethylenically unsaturated polymerizable compound, and (2) a compound having the formula:

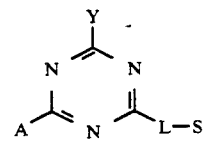

wherein
- A represents a member selected from the group consisting of mono-, di- and trihalomethyl groups,
- Y represents a member selected from the group consisting of A, L-S, $NH_2$, NHR, $NR_2$, OR, and R', where R alkyl group, or a substituted or unsubstituted aryl group, R' represents a substituted or unsubstituted alkyl group, a substituted or unsubstituted aryl group, a substituted or unsubstituted alkyl group, or a substituted or unsubstituted heterocyclic aromatic group,
- S represents a sensitizer moiety not being part of the triazine chromophores and being capable of absorbing actinic radiation, said sensitizer moiety having a λmax of at least 330 nm, and
- L represents a group linking the sensitizer moiety to the triazine nucleus, provided that the chromophore of said triazine nucleus is not attached to the chromophore of said sensitizer moiety either directly by a covalent bond or by a conjugated linkage, the portion of L directly attached to the triazine nucleus being selected from (a) carbon atom, (b) amino group selected from the group consisting of (1) aminoaryl groups wherein the nitrogen atom of the amino group is attached to the triazine nucleus and (2) an amino group wherein the nitrogen atom of the amino group is attached to both the triazine nucleus and the carbon atom of at least one

group, and (c) oxygen atom.

2. The composition of claim 1 wherein A represents a trihalomethyl group.

3. The composition of claim 2 wherein the trihalomethyl group is a member selected from the group consisting of trichloromethyl, tribromomethyl, and triiodomethyl.

4. The composition of claim 3 wherein the trihalomethyl group is a member selected from the group consisting of trichloromethyl and tribromomethyl.

5. The composition of claim 1 wherein Y represents A.

6. The composition of claim 1 wherein Y represents L-S.

7. The composition of claim 1 wherein R' represents a substituted or unsubstituted aryl group.

8. The composition of claim 1 wherein R' represent a substituted or unsubstituted heterocyclic aromatic group.

9. The composition of claim 1 wherein R' represents a substituted or unsubstituted alkenyl group.

10. The composition of claim 1 wherein S represents a cyanine group, a carbocyanine group, a styryl group, an acridine group, a polycyclic aromatic hydrocarbon group, a polyarylamine group, or an amino-substituted chalcone group.

11. The composition of claim 1 wherein the carbon atom of the portion of said linking group directly attached to the triazine nucleus is a member of the group selected from the group consisting of alkyl groups, aliphatic groups, alkenyl groups, aryl group, styryl groups, ester groups ($-CO_2-$), and combinations of the foregoing.

12. The composition of claim 1 wherein said ethylenically unsaturated polymerizable compound contains at least one acrylate group.

13. The composition of claim 1 wherein said ethylenically unsaturated polymerizable compound contains at least one methacrylate group.

14. The composition of claim 1 wherein said ehtylenically unsaturated polymerizable compound contains at least one acrylamide group.

15. The composition of claim 1 wherein for every 100 parts by weight of polymerizable compound there are from 0.005 to 10 parts by weight of said halomethyl-1,3,5-triazine compound.

16. A photosensitive element comprising a support having on at least one major surface thereof the composition of claim 1.

17. The element of claim 16 wherein said support is made of a metal.

18. The element of claim 17 wherein a said support is in the form of a plate, sheet of foil.

19. The element of claim 16 wherein said support is made of a polymer.

20. The element of claim 19 wherein said support is in the form of a plate or film.

* * * * *

UNITED STATES PATENT AND TRADEMARK OFFICE
CERTIFICATE OF CORRECTION

PATENT NO. : 5,187,045
DATED : February 16, 1993
INVENTOR(S) : Bonham et al.

It is certified that error appears in the above-indentified patent and that said Letters Patent is hereby corrected as shown below:

Col. 16, lines 16/17, "ehtylenically" should be --ethylenically--.

Col. 16, line 29, "sheet of foil" should be --sheet or foil--.

Signed and Sealed this

Twenty-fifth Day of October, 1994

Attest:

BRUCE LEHMAN

Attesting Officer

Commissioner of Patents and Trademarks